United States Patent [19]
Calvet et al.

[11] Patent Number: 5,552,313
[45] Date of Patent: Sep. 3, 1996

[54] DNA ENCODING MOUSE PHOSPHOTRIESTERASE-RELATED PROTEIN

[75] Inventors: James P. Calvet; Xiaoying Hou; Brenda S. Magenheimer; Robin L. Maser, all of Kansas City, Kans.

[73] Assignee: Kansas University, Kansas City, Kans.

[21] Appl. No.: 343,027

[22] Filed: Nov. 21, 1994

[51] Int. Cl.$^6$ .............................. C12N 1/20; C12N 9/00; C07K 1/00
[52] U.S. Cl. ....................... 435/252.33; 435/69.1; 435/172.3; 435/183; 435/320.1; 530/350; 536/23.2
[58] Field of Search .................... 435/69.1, 172.3, 435/183, 252.33, 320.1; 530/350; 536/23.2

[56] References Cited

PUBLICATIONS

Asani et al. (1991) Life Sci 49:367–374.
Deschamps et al. (1993) Comp. Biochem. Physiol. 106C:765–768.
Huang et al. (1994) Biochem. Pharmacol. 48(6): 1273–1280.
Raveh et al. (1992) Biochem. Pharmacol. 44(2): 397–400.

*Primary Examiner*—Robert A. Wax
*Assistant Examiner*—Lisa J. Hobbs
*Attorney, Agent, or Firm*—Benjamin Aaron Alder

[57] ABSTRACT

The present invention provides novel DNA sequences encoding a mouse phosphotriesterase-related protein having the sequence shown in SEQ ID NO. 12. Also provided is a phosphotriesterase-related protein having the sequence shown in SEQ ID NO. 12 and a pharmaceutical composition, comprising the protein of the present invention and a pharmaceutically acceptable carrier.

7 Claims, 8 Drawing Sheets

FIG.3

```
                                    GGCACGAGGCGGCGCACAGCGCGGAATGAAGGAAG   35
       CCCCGGAGCTGGTTAAGTAGCTGTGGACCTGGTAGGAAAGAGAAAATCCCTGAGACACTATCAGGA  101

ATGTCTTCCTTAAGTGGGAAAGTACAAACAGTTCTGGGCCTTGTAGAACCCAGCCAACTGGGACGC  167
   1  M  S  S  L  S  G  K  V  Q  T  V  L  G  L  V  E  P  S  Q  L  G  R

ACCCTGACCCACGAGCATCTGACAATGACCTTTGACAGTTTTTACTGCCCACCTCCTCCATGCCAC  233
  23  T  L  T  H  E  H  L  T  M  T  F  D  S  F  Y  C  P  P  P  P  C  H

GAAGTCACCTCCAAGGAACCTATCATGATGAAAAATCTATTTTGGATTCAGAAAAACCCCTATTCC  299
  45  E  V  T  S  K  E  P  I  M  M  K  N  L  F  W  I  Q  K  N  P  Y  S

CATCGAGAGAACCTTCAGTTGAATCAGGAGGTAGGAGCCATAAGAGAAGAGCTGTTGTATTTCAAG  365
  67  H  R  E  N  L  Q  L  N  Q  E  V  G  A  I  R  E  E  L  L  Y  F  K

GCTAAGGGCGGAGGAGCCTTGGTGGAGAATACGACAACTGGGCTCAGCAGGGACGTGCATACGCTG  431
  89  A  K  G  G  G  A  L  V  E  N  T  T  T  G  L  S  R  D  V  H  T  L

AAGTGGCTGGCAGAGCAGACTGGAGTCCACATCATAGCTGGAGCTGGGTTTTATGTTGATGCAACT  497
 111  K  W  L  A  E  Q  T  G  V  H  I  I  A  G  A  G  F  Y  V  D  A  T

CACTCTGCAGCAACCAGAGCCATGTCAGTGGAGCAGCTTACAGATGTCCTTATTAATGAAATTCTC  563
 133  H  S  A  A  T  R  A  M  S  V  E  Q  L  T  D  V  L  I  N  E  I  L

CATGGAGCTGATGGCACCAGCATCAAGTGTGGAGTTATTGGAGAAATTGGCTGCTCCTGGCCTTTG  629
 155  H  G  A  D  G  T  S  I  K  C  G  V  I  G  E  I  G  C  S  W  P  L

ACTGACAGCGAGAGAAAGATACTTGAGGCTACAGCTCACGCCCAGGCTCAGCTTGGCTGTCCTGTC  695
 177  T  D  S  E  R  K  I  L  E  A  T  A  H  A  Q  A  Q  L  G  C  P  V

ATCATCCATCCTGGACGGAACCCAGGTGCACCATTCCAGATAATCCGTATACTGCAAGAAGCAGGA  761
 199  I  I  H  P  G  R  N  P  G  A  P  F  Q  I  I  R  I  L  Q  E  A  G

GCAGACATCTCCAAAACAGTCATGTCCCACCTTGACAGGACTATATTTGATAAGAAAGAGCTGCTG  827
 221  A  D  I  S  K  T  V  M  S  H  L  D  R  T  I  F  D  K  K  E  L  L

GAGTTTGCTCAACTTGGCTGCTACTTGGAATACGATCTCTTTGGTACGGAACTCCTTAATTACCAG  893
 243  E  F  A  Q  L  G  C  Y  L  E  Y  D  L  F  G  T  E  L  L  N  Y  Q

TTGAGCCCAGATATTGATATGCCTGATGATAACAAAAGAATTAGAAGGGTCCATTTTCTAGTGGAT  959
 265  L  S  P  D  I  D  M  P  D  D  N  K  R  I  R  R  V  H  F  L  V  D

GAGGGCTATGAAGATCGGATTCTCATGGCACATGACATACACACAAAGCATCGGTTGATGAAGTAC 1025
 287  E  G  Y  E  D  R  I  L  M  A  H  D  I  H  T  K  H  R  L  M  K  Y

GGAGGTCACGGCTACTCACACATCCTTACCAACATTGTTCCTAAGATGCTCCTTAGAGGTCTGACT 1091
 309  G  G  H  G  Y  S  H  I  L  T  N  I  V  P  K  M  L  L  R  G  L  T

GAGAGGGTGCTTGACAAGATACTCATAGAAAACCCTAAACAATGGCTGACTTTTAAATAGGATGGC 1157
 331  E  R  V  L  D  K  I  L  I  E  N  P  K  Q  W  L  T  F  K  *

TGTTCACGAACCCAGACCTGGAGGATACAATGAGCAGAGAATAGTTGGTGATTTCAAATCTACTGG 1223
      AGACATTAATCCAGTCTACATAGAACTGGTGAATGGTCACTTCTCTCCTATGAGAAGCTGGATAAC 1289
      TACCACAGGGACATCTCTGGTGGGGGCCACAGGGCTCAAGTGAGTCCCATTGTCTTTCCTTAATAA 1355
      AATAAATATTGATAAAAGAGCATGTTTCCAAACAGTAGTTTAAAACTATATCCCCTAAGAATCATT 1421
      TTGGATGTCTTCCCCAACCCTGACTCTGTGATCTGCACTACTTGAGAAAAATGAAAGTGTTTCTAG 1487
      CTAAGTTGCCCCTTCTGGAGCAACCTAATGTTTCTTGTAATATTGATGATCCTACTAATTATCCTG 1553
      CTGTTCTTTAATTAATGCTTAATGAATAATATGGCATTTTAAAATCACTTTTGCAACAAGGGAAGT 1619
      TAAATTTTGAGACATTTTTTCCCAAAGGAGACTGCAATAAAATTACCAATTCACAACAATAAAGAA 1685
      ATTTCGAAGGTT                                                       1697
```

FIG.6

```
  1 ................MSSLSG............KVQTVLGLVEPSQLG  21
                   :::|.|            :::.|| | :. |: |
  1 MQTRRVVLKSAAAAGTLLGGLAGCASVAGSIGTGDRINTVRGPITISEAG  50

22 RTLTHEHLTMTFDSFYCPPPPCHEVTSKEPIMMKNLFWIQKNPYSHRENL  71
    |||||||:. . .:|                   ::  .: ::  |..|
 51 FTLTHEHICGSSAGF....................LRAWPEFFGSRKAL  79

72 QLNQEVGAIREELLYFKAKGGGALVENTTTGLSRDVHTLKWLAEQTGVHI 121
    .. | |.    :| |. .:|: .| :::||| |  : ..:|||
 80 AEKAVRGLRRA.....RAAGVRTIVDVSTFDIGRDVSLLAEVSRAADVHI 124

122 IAGAGFYVDATHSAATRAMSVEQLTDVLINEILHGADGTSIKCGVIGEIG 171
    :|..|:..|:. |  | .|||:||:.:..|| .| ::|:|:..|:| ...
125 VAATGLWFDPPLS..MRLRSVEELTQFFLREIQYGIEDTGIRAGII.KVA 171

172 CSWPLTDSERKILEATAHAQAQLGCPVIIHPGRNPGAPFQIIRILQEAGA 221
    .. .|. :  :|.|.|:|  .|.||.|.:    |     |  |:...|
172 TTGKATPFQELVLKAAARASLATGVPVTTHTAASQRDGEQQAAIFESEGL 221

222 DISKTVMSHLDRTIFDKKELLEFAQLGCYLEYDLFGTELLNYQ....LSP 267
    . |:...:| |.| | |.| .:|. |:::..|  . ...:    |:
222 SPSRVCIGHSDDTD.DLSYLTALAARGYLIGLDHIPHSAIGLEDNASASA 270

268 DIDMPDDNKRIRRVHFLVDEGYEDRILMAHD.........IHTKHRLMKY 308
    ::::.. ..|  :. |:|:||  ..||:..|         .:...  : :
271 LLGIRSWQTRALLIKALIDQGYMKQILVSNDWLFGFSSYVTNIMDVMDRV 320

309 GGHGYSHILTNIVPKMLLRGLTERVLDKILIENPKQWL...TFK.. 349
    ...| . | ..:| :  :|:.: .|. |  :.||  .:|  |::
321 NPDGMAFIPLRVIPFLREKGVPQETLAGITVTNPARFLSPTLRAS 365
```

DNA ENCODING MOUSE PHOSPHOTRIESTERASE-RELATED PROTEIN

BACKGROUND OF THE INVENTION

1. Field of the Invention

The present invention relates generally to the fields of molecular biology and genetics. More specifically, the present invention relates to a novel DNA sequences encoding a mouse phosphotriesterase-related protein and novel uses thereof.

2. Description of the Related Art

Polycystic kidney disease (PKD) is characterized by the development of innumerable, large, fluid-filled cysts from the nephrons and collecting ducts of affected kidneys. Enlargement of cysts is thought to interfere with functioning of the normal renal parenchyma, which eventually leads to renal failure. In humans, PKD can be inherited as an autosomal dominant (ADPKD) or an autosomal recessive trait (ARPKD). ADPKD is a common disease, affecting 1 in 500–1,000 individuals, and contributes significantly to the number of patients on long-term dialysis. ARPKD is less common, occurring in 1 in every 6,000–14,000 live births, but is usually fatal in infancy. To date, the factors causing the initiation of renal cysts and their progressive enlargement, and the development of azotemia and renal failure are not known. Biochemical and histological studies have identified characteristics common to all cysts in polycystic kidney disease: abnormal cell proliferation, basement membrane alterations, and changes in cell polarity and transport or secretion. Considerable work has focused on the potential involvement of these factors in cyst formation and progression toward renal failure. Genetic approaches also have been utilized to identify the defective gene(s) in this disease in hopes of determining the primary defect in PKD. Although a number of genes showing abnormal expression PKD in human and animal models have been identified. The relationship of these genes and the common characteristics of renal cysts is not apparent.

The C57BL/6J-cpk mouse has been utilized as a model for human ARPKD. PKD in this animal model is inherited as an autosomal recessive trait and is characterized by the rapid development primarily of collecting duct cysts resulting in renal failure and death of the affected mice by 3–4 weeks of age. The cpk gene has been mapped to mouse chromsome 12, but has not been isolated and identified. Previous work has demonstrated the abnormal expression of different genes in the polycystic kidneys of cpk mice. These genes include the proto-oncogenes, c-fos, c-myc, and c-K1-ras; preproEGF; histone H4; beta-actin; and the developmentally regulated gene, sulfated glycoprotein 2 (SGP-2).

Nephrotoxic injury causes kidney tubule damage and necrosis, followed by repair of the damage and regeneration of normal renal function. Folic acid in high concentrations causes renal injury and is one of the most potent known stimuli for cell proliferation in the rodent kidney. The administration of a single large dose of folic acid by intraperitoneal injection is followed within hours by evidence of decreasing kidney function and by a number of cellular and molecular events consistent with the onset of kidney regeneration. Following folic acid-induced acute renal injury, there is an increased rate of cell division. The early phase of the response to folic acid treatment is an ordered sequence of expression of cell-cycle specific genes. There is a rapid and transient increase in the level of c-fos mRNA which peaks at 3 hours following folic acid treatment, followed by increases in c-myc, c-Ki-ras, c-Ha-ras and beta-actin mRNAs. These events precede or coincide with an increase in histone H4 mRNA at 24–36 hours following folic acid treatment. The temporal pattern of induction of these mRNAs suggests that the kidney responds very rapidly to folic acid, followed by the synchronized progression of kidney cells through the G1 phase of the cell cycle and ultimately through cell division. Renal injury has been shown to cause changes in the expression of a number of genes, including early response and cell cycle-regulated genes (c-fos, JE, KC, egr-1, c-myc, c-Ki-ras, c-Ha-ras, beta-actin, histones H2b and H4), growth factors and their receptors (HGF, c-met, EGF), the enzyme superoxide dismutase, and secreted proteins (renin, endothelin, Tamm-horsfall/uromodulin, SGP-2/clusterin/TRPM-2). While some of these genes appear to be associated with the cell proliferation required for kidney repair, a decrease in EGF or, an increase in SGP-2 has no known role in the injury process or in the subsequent regeneration.

The bacterial phosphotriesterases from Flavobacterium and *Pseudoraonas diminuta* are enzymes encoded by naturally occurring plasmids found in these two organisms. The protein coding regions of the genes in these two bacterial species are identical at the nucleotide sequence and amino acid sequence levels. The protein is a zinc metalloenzyme that has a broad substrate specificity, catalyzing the hydrolysis of organophosphate-triester compounds. Among the substrates of the enzyme are the insecticides parathion and paraoxon, and they have received a great deal of attention for their possible industrial, agricultural, and medical applications as a possible detoxifying enzyme or enzyme that may confer protection to a toxic overdose of organophosphates. The enzyme goes by a variety of names including parathion hydrolase, organophosphorous acid anhydrase, aryldialkylphosphatase and phosphotriesterase. There is no known eukaryotic protein that is structurally or evolutionarily related to the Flavobacterium/Pseudomonas enzyme.

Arylesterases that degrade paraoxon have been isolated from liver microsomes and cytosol and from blood plasma of human, rabbit and rat. These enzymes, called paraoxonases, are synthesized predominantly, if not exclusively, in the liver and have different properties from the bacterial parathion hydrolase (phosphotriesterase). Furthermore, the human and rabbit cDNAs for serum paraoxonase/arylesterase have been isolated and characterized and are unrelated to both the Flavobacterium or Pseudomonas phosphotriesterase.

The prior art is deficient in the lack of effective means of detecting the polycystic kidney disease and renal failure. The present invention fulfills this longstanding need and desire in the art.

SUMMARY OF THE INVENTION

The present invention provides the cloning and characterization of a mouse kidney- and liver-expressed cDNA having homology with a prokaryotic parathion hydrolase (phosphotriesterase) sequence. Furthermore, the present invention demonstrates that this gene has an abnormal expression in cystic kidneys of the recessive cpk murine model of polycystic kidney disease and has decreased expression following acute renal injury.

In one embodiment of the present invention, there is provided DNA sequences encoding a mouse phosphotriesterase-related protein having the sequence shown in SEQ ID NO. 12.

In another embodiment of the present invention, there is provided the DNA of claim 1, wherein said DNA has the sequence shown in SEQ ID NO. 1.

In yet another embodiment of the present invention, there is provided a phosphotriesterase-related protein having the sequence shown in SEQ ID NO. 12.

In still yet another embodiment of the present invention, there is provided pharmaceutical composition, comprising the protein of claim 3 and a pharmaceutically acceptable carrier.

In another embodiment of the present invention, there is provided a vector comprising a DNA sequence coding for a mouse phosphotriesterase-related protein and said vector is capable of replication in a host which comprises, in operable linkage: a) an origin of replication; b) a promoter; and c) a DNA sequence coding for said protein.

In another embodiment of the present invention, there is provided a host transformed with a recombinant DNA molecule, wherein said recombinant DNA molecule comprises a DNA sequence having the sequence of SEQ ID No. 1.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows the complete nucleotide sequence of the 56-1 cDNAs (clones 35-2 and 46-2) and the deduced amino acid sequence of mpr56-1.

FIG. 6 shows the optimal pairwise alignment analysis of mouse mpr56-1 and bacterial parathion hydrolase (phosphotriesterase). Analysis was carried out using the GAP program (Genetics Computer Group, Inc., Madison, Wis.) and default parameters of 3.0 for a gap weight and 0.1 for a length weight. The full-length mouse (upper line) and Flavobacterium (lower line) proteins are shown. The quality of the match was 162.4 compared to an average quality based on ten randomizations of 109.2 +/–4.6. The sequences have a similarity of 51% and an identity of 27%. The values used in the alignments were based on a normalized Dayhoff PAM-250 log-odds mutational distance matrix in which a perfect match (|) is 1.5, a close match (:) is ≧0.5, and an acceptable match (.) is ≧0.1.

DETAILED DESCRIPTION OF THE INVENTION

Figure 1:
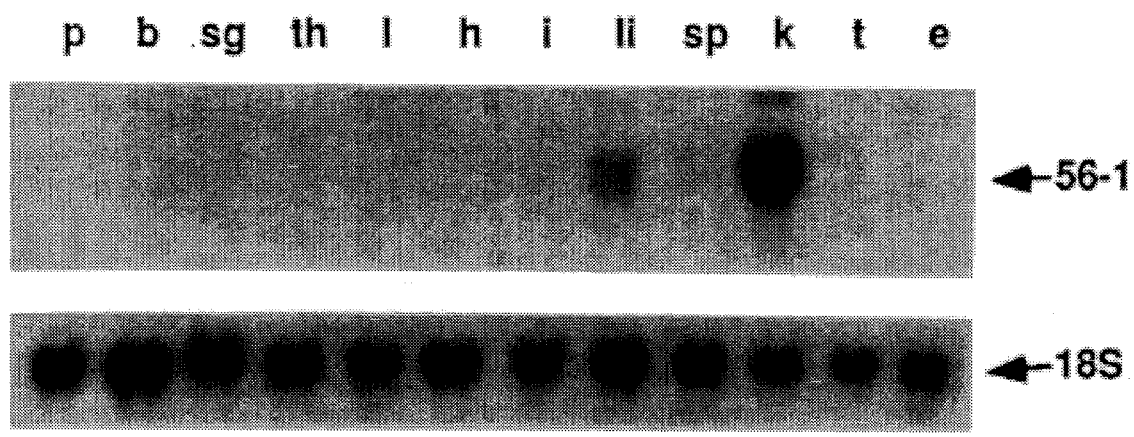
FIG. 1 shows the expression of mpr56-1 mRNA in various mouse organs. Northern blot hybridization with an mpr56-1 (56-1) riboprobe to total RNA from a number of mouse organs: (p) pancreas, (b) brain, (sg) salivary gland, (th) thymus, (l) lung, (h) heart, (i) intestine, (li) liver, (sp) spleen, (k) kidney, (t) testis, and (e) epididymis. Each of the samples was also hybridized with an 18S rRNA (18S) oligonucleotide probe to demonstrate the amount of RNA on the blot.

To illustrate abnormalities in cell growth and differentiation associated with cyst formation in polycystic kidney disease, differential cDNA library screening was carried out using cDNA libraries constructed with the RNA of normal and cystic kidneys from the recessive C57BL/6J-cpk mouse. It is unknown whether there is a wide range or a limited number of genes affected in PKD; it is unknown whether there are classes of genes affected; and it is unknown whether there is a range of differential expression between normal and cystic kidneys. cDNA libraries were constructed from normal and cystic kidneys of 3-week-old cpk mice, followed by differential screening of the libraries using probes generated from normal and cystic kidney RNA. After screening of 60,000 recombinant plaques, over 50 different differentially expressed mRNAs were identified representing genes corresponding to general housekeeping, glycolytic/gluconeogenic, oxidant stress protection and cell adhesion proteins. In addition, a number of clones corresponding to unknown proteins expressed in kidney were isolated. The level of differential expression of 29 of these mRNAs was determined to range from more than 14-fold underexpression to greater than 6-fold overexpression in cystic kidneys from 3-week-old cpk mice. The expression of one of the differentially expressed genes, encoding plasma glutathione peroxidase was further characterized and found to have a role in the development of azotemia and/or renal failure. The pattern of differential expression of many of the genes was found to be consistent with that expected for cystic kidneys having an immature phenotype, suggesting that loss of renal function and progression to renal failure may be a result of injury-induced dedifferentiation or lack of terminal differentiation. Among a number of genes found to be abnormally expressed in cystic kidneys was one that showed very significant underexpression. Because the expression of this gene of the present invention appeared to be severely affected by the disease and because initial database searches were unsuccessful in identifying it, the cDNA (clone 56-1) was selected for further analysis ultimately to identify the gene and to determine its function in the kidney and its role in polycystic kidney disease.

Hybridization analyses revealed that the mRNA is expressed primarily in kidney proximal tubules and liver, and that the kidney expression begins postnatally and continues in the adult. Expression of this mRNA was found to be significantly decreased upon acute renal injury induced by a single intraperitoneal injection of folic acid, and mRNA expression returned to normal upon recovery of kidney function. The sequence of the cDNA predicted a protein of 349 amino acids, which was confirmed by in vitro translation of a sense-strand transcript, producing a protein of approximately 39 kd. While searches of the nucleic acid databases with the cDNA sequence found no matches, the amino acid sequence showed similarity with Flavobacterium parathion hydrolase (phosphotriesterase) encoded by the organophosphate-degrading gene. This enzyme hydrolyzes toxic organophosphates and other phosphotriesters. Use of optimal alignment programs demonstrated a significant overall homology between the bacterial and mouse sequences, with approximately 50% amino acid sequence similarity. This cDNA represents the first eukaryotic sequence showing similarity to the prokaryotic organophosphate-degrading gene. Thus, the protein of the present invention is named mpr56-1 (mouse phosphotriesterase-related protein 56-1).

The present invention is directed to DNA sequences encoding a mouse phosphotriesterase-related protein having the sequence shown in SEQ ID NO. 12. A person having ordinary skill in this art would readily recognize that minor modifications may be made to the mouse phosphotriesterase-related DNA of the present invention while still encoding the same protein. Preferably, the DNA has the sequence shown in SEQ ID NO. 1. The present invention also provides a phosphotriesterase-related protein having the sequence shown in SEQ ID NO. 12.

It is specifically contemplated that pharmaceutical compositions may be prepared using the novel protein of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel protein of the present invention.

The level of ordinary skill of the average scientist in the area of molecular biology has increased substantially in recent years. A person having ordinary skill in this art would readily be able to raise polyclonal or monoclonal antibodies to the novel protein of the present invention given the teachings herein. With such an antibody, one with ordinary skill in this art would be able to measure the amount of the mouse phosphotriesterase-related protein in the body. Such a measurement would be a useful diagnostic marker of polycystic kidney disease or acute renal failure.

Knowledge of the mouse phosphotriesterase-related sequence will permit other mammalian genes and cDNAs to be isolated by using the mouse DNA as a hybridization probe to screen recombinant DNA libraries from other organisms, or by using an antibody to the mouse protein to screen protein expression libraries. Having genes or cDNAs from other organisms helps in determining the protein's functions and provide better reagents for human use.

The mouse mpr56-1 protein can be made by translation in an in vitro system or by expression of a suitably constructed clone for in vivo production in a prokaryotic or eukaryotic host cell. Hydrolase activity is assayed by incubating the purified protein with parathion or paraoxon. The products of hydrolysis would include p-nitrophenol, which are readily detected by absorbance spectroscopy. There are other organophosphate substances that are also tested to determine the range of specificity of the enzyme, to determine if the activities of the mpr56-1 protein overlap with those of other esterases or hydrolases.

As used herein, the term "host" is meant to include not only prokaryotes but also eukaryotes such as yeast, plant and animal cells. A recombinant DNA molecule coding for the mouse phosphotriesterase-related protein of the present invention can be used to transform a host using any of the techniques commonly known to those of ordinary skill in the art. Especially preferred is the use of a vector containing coding sequences for the mouse phosphotriesterase-related protein of the present invention for purposes of prokaryote transformation.

Prokaryotic hosts may include *E. coli, S. tymphimurium, Serratia marcescens* and *Bacillus subtilis*. Eukaryotic hosts may include yeasts such as *Pichia pastoris* or mammalian cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The present invention also comprises a vector comprising a DNA sequence coding for a mouse phosphotriesterase-related protein and said vector is capable of replication in a host which comprises, in operable linkage: a) an origin of replication; b) a promoter; and c) a DNA sequence coding for said protein. Preferably, the vector of the present invention contains the DNA sequence shown in SEQ ID No. 1.

The present invention also comprises a host transformed with a recombinant DNA molecule, wherein said recombinant DNA molecule comprises a DNA sequence having the sequence of SEQ ID No. 1. A representative example of a host which may be transformed using the teachings herein is *E. coli*. An *E. coli* host transfected with a plasmid containing the recombinant DNA of the present was deposited with the American Type Culture Collection as Accession number 69712 on Nov. 9, 1994.

The following examples are given for the purpose of illustrating various embodiments of the invention and are not meant to limit the present invention in any fashion.

EXAMPLE 1

Animals and RNA isolation

C57BL/6J-cpk mice were maintained as a breeding colony at the University of Kansas Medical Center. Total RNA from various fetal through adult mouse organs was isolated by the GITC/phenol/chloroform or the GITC/CsCl methods. Poly(A)+ RNA was prepared by one round of oligo(dT) chromatography. For acute renal failure, adult CF-1 mice weighing 25–30 grams were injected intraperitoneally (i.p.) with 200 mg/kg (body weight) folic acid in 150 mM NaHCO$_3$. Control mice received only 150 mM NaHCO$_3$.

EXAMPLE 2 cDNA library construction and differential screening cDNAs were constructed by oligo(dT) priming of poly(A)+ RNA isolated from normal and cystic kidneys of 3-week-old C57BL/6J-cpk mice and were cloned into the EcoRI site of the lambda gt11 vector (Stratagene). Both the normal and the cystic cDNA libraries were determined to represent statistically complete libraries containing $2.1 \times 10^6$ and $5.8 \times 10^7$ recombinant clones, respectively. Duplicate plaque lifts using Biotrans+ filters with, ~800 plaques/plate from either library were pre-hybridized in 6X SSD (0.9 M NaCl, 90 mM Na$_3$ citrate, 10 mM Na phosphate buffer pH 7.0, 0.2% SDS, 0.02% Ficoll, 0.02% polyvinylpyrrolidone, 0.02% bovine serum albumin) and 50 μg/ml yeast tRNA for 3 hrs at 65° C. and then hybridized for 48 hours at 65° C. in pre-hybridization buffer plus $10^5$–$10^6$ cpm/ml of either [$\gamma$-$^{32}$P]ATP-kinased, hydrolyzed RNA or [$\gamma$-$^{32}$P]dCTP-labeled, oligo(dT)-primed single-stranded cDNA probes prepared from poly(A)+ RNA from normal and cystic kidneys of 3-week-old cpk mice. The duplicate lifts were washed in 6X SSD at 65° C. for 3 hours and exposed to film for 1–14 days with intensifying screens (NEN-DuPont). Plaques showing differential hybridization with the normal and cystic probes were picked frown the master plates and stored in SM buffer (50 mM Tris pH 7.5, 100 mM NaCl, 8 mM MgSO$_4$, 0.01% gelatin).

EXAMPLE 3

Differential Southern analysis, cDNA subcloning, and DNA sequencing

The cDNA inserts in lambda gt11 were amplified by PCR using lambda gt11 forward and reverse primers (Boehringer Mannheim) and were used for differential Southern hybridization analysis and for subcloning. Differential Southern hybridization analysis involves electrophoresis of equal amounts of each cDNA-PCR product on duplicate agarose gels with appropriate controls (cDNA inserts whose differential expression in 3-week normal versus cystic kidneys is known), and Southern blotting of duplicate gels followed by hybridization with the normal and cystic probes. cDNA-PCR products demonstrating differential hybridization in the Southern analyses were non-directionally subcloned into either the SmaI or EcoRI site of pGem3zf+ (Promega) or pBluescript KS+ (Stratagene) and were used for DNA sequencing analysis and riboprobe synthesis for Northern blot hybridization. DNA sequencing was performed with single-stranded (pGem subclones) or double-stranded (pBluescript subclones) DNA templates using Sequenase 2.0 (USB) and M13-40 (USB), T3 and/or T7 (Boehringer Mannheim) sequencing primers. The GenBank/EMBL nucleotide sequence database was searched using BLASTN to identify the differentially expressed genes.

EXAMPLE 4

Isolation of full-length 56-1 cDNA clones and DNA sequencing

An ~170 base pair EcoRI-TaqI fragment was isolated from the 5'-end of the original 56-1 clone (containing an ~1.6 kb PCR-amplified cDNA insert subcloned into the EcoRI site of pBluescript KS) and was used to generate a $^{32}$P-random primer-labeled probe that was subsequently used to screen a 3-week normal kidney library in Lambda ZAP XR (courtesy of C. Rankin) for full-length (and non-PCR-generated) 56-1 clones. Screening resulted in the isolation of two clones, designated 35-2 and 46-2, containing approximately 1.7 kb and 1.6 kb inserts, respectively, which were in vivo excised as double-stranded phagemids (using the Stratagene protocols) and used for subsequent DNA sequencing. The complete, bidirectional sequence of clone 35-2 was obtained by constructing 5' and 3' deletion clones using convenient restriction sites and by synthesizing sequencing primers. Sequencing reactions using dITP in place of dGTP were performed as necessary to eliminate gel compression artifacts. Four deletion clones were constructed as follows. A 500 base pair PstI restriction fragment was removed from clone 35-2 (using PstI sites at nucleotide 507 in clone 35-2 and in the multiple cloning site of pBluescript), and the digested clone was religated to generate deletion clone 35-2D. Deletion clone 35-2dell was generated by subcloning an end-filled internal 495 base pair AccI fragment (nucleotides 743–1238 in the full-length sequence) into the SmaI site of pBluescript. 35-2de12 was generated by digesting clone 35-2 with AccI and EcoRI (removing the 5'–1238 base pairs of 35-2), followed by end-filling and re-ligation. The fragment 35-2del3 was generated by digesting clone 35-2 with AccI and XhoI (removing the 3'–954 base pairs of 35-2), followed by end-filling and re-ligation. The following primers were synthesized and used for DNA sequencing: 46-2 primer (5'-GCCATAAGAGAAGAGCTG-3'), identical to nucleotides 336–353 in the full-length sequence; P1 (5'-CAAGTAGTGCAGATCACAG-3'), complementary to nucleotides 1447–1465; P2 (5'-AGGCTCAGCTTGGCTGT-3'), identical to nucleotides 673–689; P3 (5'-CAAGTGAGTCCCATTGTC-3'), identical to nucleotides 1326–1343; P4 (5'-GACATCTCCAAAACAG-3'), identical to nucleotides 765–780; P5 (5'-ACAGCCAAGCTGAGCCT-3'), complementary to nucleotides 673–689; P6 (5'-GTC6TATTCTCCACCAA-3'), complementary to nucleotides 384–400; P7 (5'-GATGAGGGCTATGAAGAT-3'), identical to nucleotides 957–974; and P8 (5'-GTATGTCATGTGCCATGA-3'), complementary to nucleotides 982–999.

EXAMPLE 5

Northern blot analysis

Northern blots were prepared using pools of RNA representing at least 10 mice in order to reduce the effects of individual variation. Northern blot hybridizations were repeated at least 2 times but usually 3 or 4 times. Between 2.5 μg and 10 μg of RNA was electrophoresed in 2.2 M formaldehyde gels and the gels were stained, photographed, and blotted to GeneScreenPlus membranes (NEN-DuPont). cDNA subclones were linearized for synthesis of [$\gamma$-$^{32}$P] CTP-labeled antisense riboprobes using SP6, T7, or T3 RNA polymerase. Blots were pre-hybridized in 1 M NaCl, 1% SDS, 40% formamide, 0.5% dextran sulfate, and 50 μg/ml yeast tRNA for 3 hours at 65° C., and then hybridized in pre-hybridization buffer containing $10^6$ cpm/ml cRNA probe for 14–18 hours at 65° C. Blots were washed for 1 hour in 0.3X SSC, 0.1% SDS at 65° C. and twice for 1 hour in 0.1X SSC, 0.1% SDS at 65° C., and exposed to film with or without intensifying screens. Controls for equal loading and blotting of RNA were performed by stripping blots and re-hybridizing with a [γ-$^{32}$P]ATP-labeled 18S oligomer probe.

EXAMPLE 6

In situ hybridization analysis

Frozen sections of 3-week kidneys were hybridized with an [γ-$^{35}$S]CTP-labeled antisense riboprobe generated by T7 RNA polymerase transcription of AccI-linearized clone 35-2 (including the 5'-most 743 nucleotides of the sequence).

EXAMPLE 7

Primer extension analysis

The primer extension assay was modified from Boorstein and Craig (1989). The primer [5'-AAGGCCCAGAACT-GTTTGTAC-3'; specific for nucleotides 123–143 of clone 35-2] was end-labeled by combining 20 pmol oligonucleotide, 100 μCi of [γ-$^{32}$P]ATP (3000 Ci/mmol), 1.5 μl of 10X kinase buffer (kinase buffer), and H$_2$O to a final volume of 14 μl, with 1 μl of T4 polynucleotide kinase (8 units/μl, Promega) and incubating 30 minutes at 37° C. The end-labeled product was purified by Nuctrap Push-column (Stratagene). Poly(A)+ RNA (10 μg) from mouse liver was mixed with 2 μl of 5X annealing buffer (1.5 M KCl, 50 mM Tris-HCl, pH 7.5, 10 mM EDTA) and 0.3 pmol of labeled oligonucleotide (5×10$^6$ cpm/pmol) in a final volume of 10 μl. The mixture was incubated for 5 minutes at 85° C., then annealed at 3 hours at 52° C. 40 μl of 1.25X reaction buffer (1.25 mM of each dNTP, 12.5 mM DTT, 12.5 mM Tris-HCl, pH 8.3, 75 μg/ml Actinomycin D, 7.5 mM MgCl$_2$, 1 μl RNasin) and 2 μl of MMLV reverse transcriptase (200 units/μl, GibcoBRL) were added and the extension reaction was carried out at 37° C. for 60 minutes. After stopping the reaction with 1 μl of 0.5 M EDTA, the RNA was degraded with 6 μl of 1N NaOH at 55° C. for 1 hour. The solution was neutralized with 6 μl of 1N HCl and the products were precipitated with 2 vol ethanol and 0.1 vol ammonium acetate at −20° C. overnight. The pellet was dissolved in 4 μl of TE and mixed with 6 μl of sequencing dye. After heating to 95° C. for 5 minutes and chilling on ice, the samples were loaded (3 μl per lane) on an 8% sequencing gel together with an M13 DNA sequencing standard used as a marker. 50 μg of total kidney RNA gave the same result (data not shown).

EXAMPLE 8

In vitro translation analysis

In vitro translation was carried out using a rabbit reticulocyte lysate translation system according to the manufacturer's recommendations (GibcoBRL). 0.5 μg of in vitro transcribed sense RNA from the full-length (35-2) or truncated (46-2) clones were used together with CAT mRNA (24 kd protein product) as a control. 25 μCi of L-[$^{35}$S]methionine was added to the 30 μl reaction to generate radiolabeled in vitro synthesized proteins. Sodium dodecyl sulfate (SDS)-polyacrylamide gel electrophoresis was carried out according to the manufacturer's protocols. After electrophoresis, the gels were fixed, dried, and exposed to X-ray film at −70° C.

EXAMPLE 9

Expression of clone 56-1

Approximately 60,000 recombinant cDNA clones were differentially screened using cDNA libraries constructed with the RNA of normal and cystic kidneys from the recessive C57BL/6J-cpk mouse. One clone, 56-1, was partially sequenced, and at the nucleic acid level showed no significant match in the databases. This clone was then used to generate an antisense riboprobe for northern analysis, which indicated that the 56-1 mRNA was about 2 kb in length and approximately 12.5-fold or 92% decreased in cystic kidneys. Northern hybridization with RNAs from a number of mouse tissues indicated that 56-1 mRNA is expressed at high levels in kidney and somewhat lower levels in liver (FIG. 1). Based on its novel sequence, high kidney and liver expression, and significantly decreased mRNA levels in cystic kidneys, this cDNA was selected for further analysis.

EXAMPLE 10

Sequencing of clones

Figure 2:
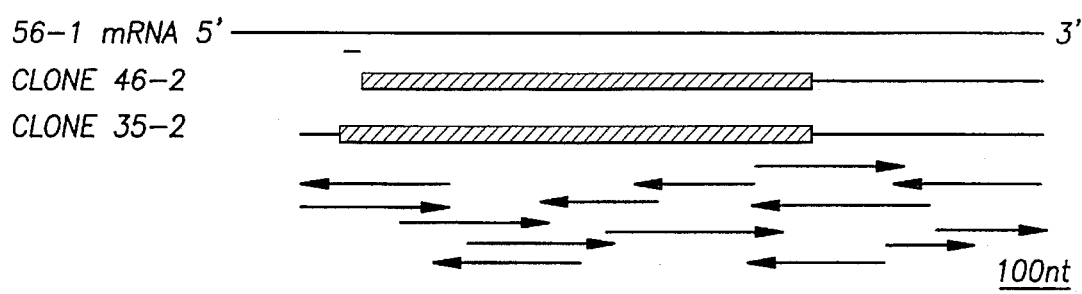
FIG. 2 illustrates the sequencing strategy used to obtain the mpr56-1 cDNA clones of the present invention. The two cDNA clones used for sequencing, clone 46-2 and clone 35-2, are shown below 56-1 mRNA, with the forward and reverse sequences indicated by arrows. The large open reading frame is shown by the filled boxes, and the position of the primer used in the primer extension analysis is shown by the short line close to the 5' end of the open reading frame.

The initial 56-1 clone, which represented approximately 1.6 kb at the 3' end of the mRNA, was used to screen a kidney cDNA library in Lambda ZAP for full-length cDNA clones. The longest clones isolated from this screening are shown in FIG. 2, in relation to 56-1 mRNA. Sequencing of clone 46-2 revealed a long open reading frame starting at the very 5' end of the cDNA. Sequencing of clone 35-2 revealed an AUG codon at the 5' end of the open reading frame and an upstream, in-frame termination codon. As shown in FIG. 3, the cDNA has a 1047 base pair open reading frame.

Figure 4:
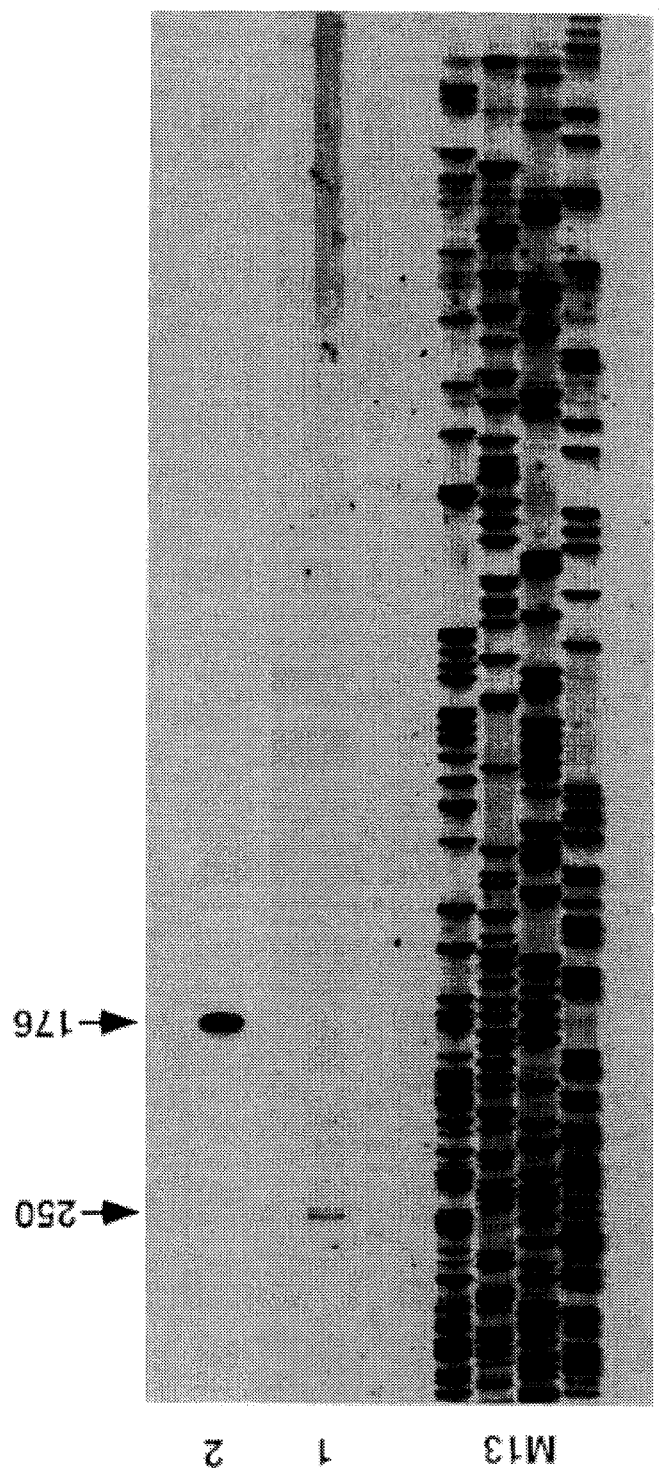
FIG. 4 shows the primer extension analysis of mpr56-1 mRNA. Lane 1 contains the primer extension products from mouse liver poly(A)+ RNA; lane 2 contains the primer extension products from a sense-strand control RNA transcribed from clone 35-2. A set of M13 sequencing reactions is shown on the left (in the order G,A,T,C). Position 176 in the M13 sequence corresponds to an extension product of 216 bases (176 nucleotides plus 40 nucleotides to the M13 primer site). Position 250 corresponds to an extension product that is 74 nucleotides longer than the control sequence.

Primer extension was carried out to determine the full length of the mRNA. A primer was generated to a sequence within the open reading frame (nucleotides 22–42 from the AUG codon) 143 base pairs from the 5' end of clone 35-2 (FIGS. 2 and 3). As a positive control, a sense-strand transcript was synthesized from clone 35-2 using T3 RNA polymerase. As shown in FIG. 4 (lane 2), a single band was obtained with the 35-2 transcript (at position 176 in the M13 sequence). Since the −40 primer was used for the M13 sequence, the band in lane 2 corresponds to an extension product from the sense-strand transcript of 216 bases (176 nucleotides plus 40 nucleotides). This product is comprised of 143 bases from the 35-2 cDNA (101 nucleotides of 5' untranslated sequence plus 42 nucleotides of translated sequence including the primer) plus 73 nucleotides of vector sequence downstream of the T3 polymerase start site.

Primer extension using total RNA from kidney (data not shown) or poly(A)+ RNA from liver showed a doublet (labeled 250) (FIG. 4, lane 1). From the stronger of the two bands, this extension product was 74 nucleotides longer than the 35-2 sense-strand control. However, since 73 nucleotides of the 35-2 control was from vector, the full-length mRNA actually goes 147 nucleotides beyond the 5' end of the 35-2 cDNA. Since 35-2 includes 101 bases of 5' untranslated sequence, the 5' untranslated region is a total of 248 bases (101 nucleotides plus 147 nucleotides). Thus, the full-length mRNA without the poly(A) tail is a total of 1844 bases, comprised of a 248 nucleotides 5' untranslated region, 1047 nucleotides open reading frame, and 549 nucleotides 3' untranslated region. This corresponds well with the size of the mRNA of about 2 kb (which would include the poly(A) tail) obtained in Northern blots. There are two canonical (AATAAA) polyadenylation sites 16–21 nucleotides (nucleotides 1677–1682) and 38–43 nucleotides (nucleotides 1655–1660) upstream of the poly(A) tail (FIG. 3). Based on the presence of the long open reading frame (making up more than half of the mRNA length) and termination codons in all three reading frames upstream of the putative AUG initiation codon, it is likely that nucleotides 102–1148 of the cDNA sequence (FIG. 3) encode a protein. This open reading frame predicts a polypeptide of 349 amino acids with a calculated molecular mass of 39,218 daltons.

EXAMPLE 11

Sequencing of clone 35-2

Figure 5:
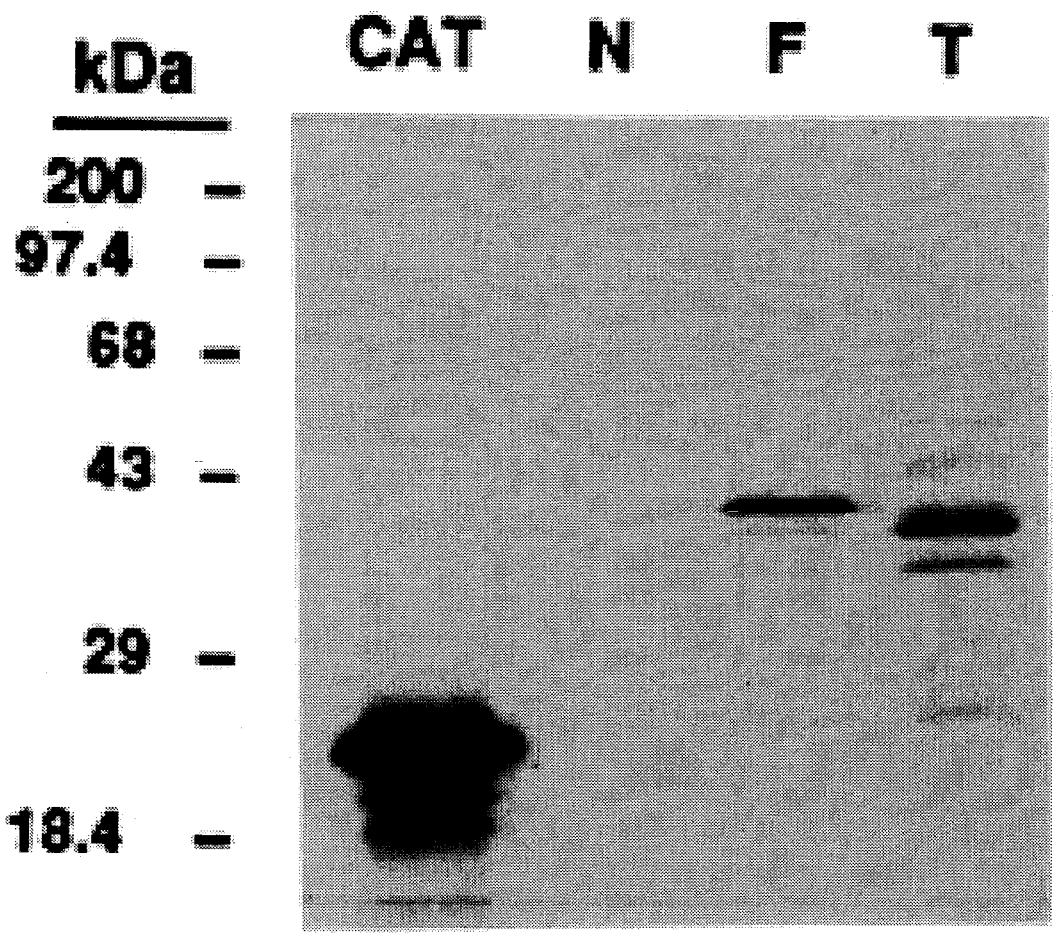
FIG. 5 shows the in vitro translation of the mpr56-1 protein. In vitro translation in a rabbit reticulocyte system was carried out with the full-length (F) and truncated (T) sense-strand, in vitro-capped RNAs transcribed from clones 35-2 and 46-2. The full-length RNA gave rise to a 39 kd protein and the truncated RNA gave rise to a major 36 kd protein and a minor 33 kd protein. Control, uncapped chloramphenicol acetyltransferase (CAT) mRNA produced a protein of 24 kd. Lane N contained no RNA; markers are shown on the left.

To determine if a protein of the predicted size can be made from the open reading frame, a sense-strand transcript of clone 35-2 was translated in vitro in a rabbit reticulocyte system. The 35-2 transcript, which contains the full-length (F) open reading frame, gave rise to a single major protein band that migrated at approximately 39 kd (FIG. 5, lane F). A sense-strand transcript of clone 46-2, which is truncated (T) at nucleotide 134 just downstream of the putative AUG initiation codon, did not produce this 39 kd band, but instead gave rise to a major band of about 36 kd and a minor band of about 33 kd (FIG. 5, lane T). This result provides evidence that the 39 kd protein was initiated at the AUG at the 5' end of the large open reading frame (nucleotide 102) (FIG. 3). Presumably, the truncated proteins in FIG. 5, lane T were due to initiation at the next available downstream AUGs at nucleotides 192 and 258/261 (FIG. 3), which would give proteins of calculated masses of 36,016 daltons and 33,508/33,377 daltons, respectively. The AUG for the full-length open reading frame is within an acceptable Kozak sequence, as are the AUGs for the truncated products.

The protein sequence predicted for the full-length clone was analyzed for structural and chemical characteristics and for sequence motifs using the PC/GENE software package. The polypeptide has an isoelectric point of 6.18 and a predicted helical content of about 46–50%. There are no regions that would suggest membrane-spanning helices and there is no evidence for an N-terminal signal sequence. The sequence has potential sites for N-glycosylation (N98), N-myristoylation (G156, G220), casein kinase II phosphorylation (T47, S66, T177, S229, T234), and protein kinase C phosphorylation (S5, T47, S66, T109, S161, S179, T330, T347).

Searches of the non-redundant nucleic acid databases with the full-length clone using FASTA or BLASTN were unable to find a significant match. Searches of the protein databases with the amino acid sequence using TBLASTN or BLASTP found a number of short matches with a Flavobacterium parathion hydrolase (phosphotriesterase) cDNA (data not shown). As these short matches were located throughout the two sequences from the N-terminus to the C-terminus, a more complete analysis was carried out. A FASTA peptide search of the SwissProt database identified this phosphotriesterase sequence as the best match. Likewise, a BLITZ search of SwissProt found a statistically significant match with this Flavobacterium sequence. Optimal pairwise alignment analysis between the full-length mouse and Flavobacterium sequences with the GAP program (Genetics Computer Group, Inc., Madison, Wis.) showed 51% similarity and 27% identity, with a quality score of 162.4 (FIG. 6). In contrast, ten randomized alignments of the sequences gave an average quality score 109.2±4.6. Thus, based on the overall quality of the alignment, the mouse 56-1 coding sequence is homologous to the Flavobacterium parathion hydrolase (phosphotriesterase) coding sequence. Because of this relationship, the 56-1 gene has been named mpr56-1 for mouse phosphotriesterase-related protein 56-1.

EXAMPLE 12

Expression of the mpr56-1 gene

Figure 7:
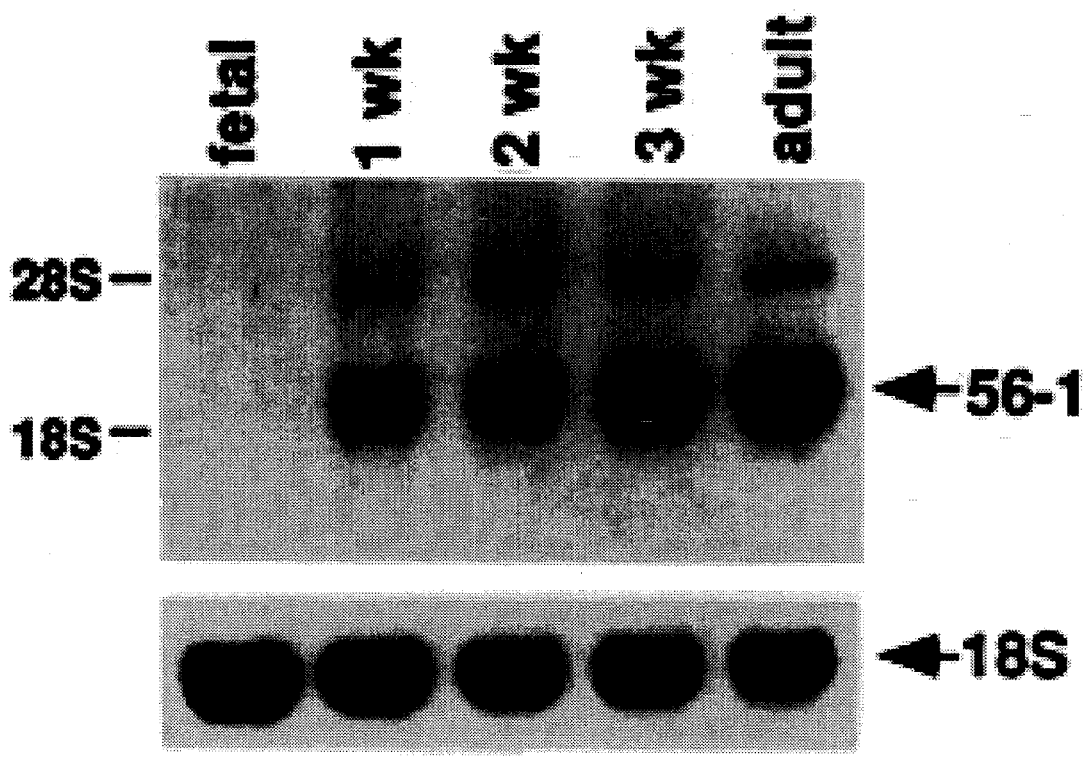
FIG. 7 shows the expression of mpr56-1 mRNA in kidney development. Northern blot hybridization with an mpr56-1 (56-1) riboprobe to total RNA from mouse fetal kidney; neonatal kidney at 1 week (1 wk), 2 weeks (2 wk), and 3 weeks (3 wk); and adult kidney. Each of the samples was also hybridized with an 18S rRNA (18S) oligonucleotide probe.
Figure 8:
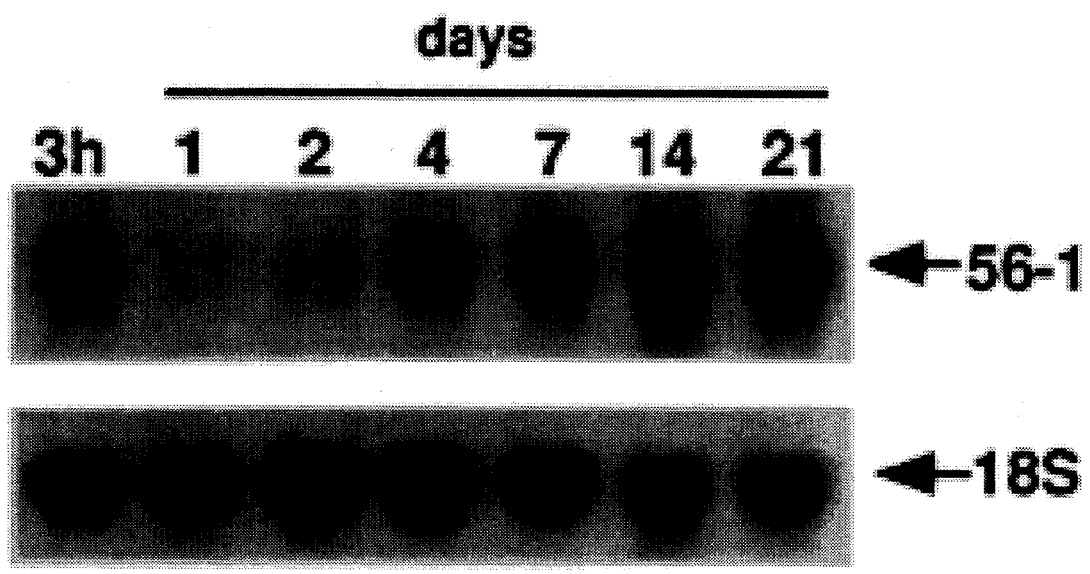
FIG. 8 shows the expression of mpr56-1 mRNA following renal injury. Northern blot hybridization with an mpr56-1 (56-1) riboprobe to total RNA from adult mouse kidneys following a single i.p. injection of folic acid. Kidneys were removed and analyzed at 3 hours (3 h) and 1–21 days following induction of renal injury. Each of the samples was also hybridized with an 18S rRNA (18S) oligonucleotide probe.

The expression of the mpr56-1 gene was examined in mouse kidney to determine when in development and where in the kidney the mRNA was expressed. As evident in the Northern blot in FIG. 7, mRNA was not present at a detectable level in fetal kidneys, but appeared 1-week after birth, continued to rise during the postnatal period, and was highest in adult kidney. To determine the localization of this expression in the kidney, in situ hybridization was carried out. The highest level of mpr56-1 mRNA expression is in proximal tubules. The expression of the mpr56-1 gene following renal injury and during recovery was also examined. As seen in FIG. 8, there was a rapid and almost complete loss of mpr56-1 mRNA by 1 day following induction of renal injury with a single i.p. injection of folic acid. The markedly decreased mRNA levels continued for 2 days and was followed by a gradual return of mpr56-1 mRNA to normal levels by 3 weeks following injury. Thus, expression of the mpr56-1 gene is particularly sensitive to injury-induced dedifferentiation in the kidney.

The identity of the DNA mouse phosphotriesterase related protein of the present invention is based on a number of criteria. It was first established that the long open reading frame has the potential to encode a polypeptide of the size predicted from the sequence. This was demonstrated by in vitro translation using a sense-strand transcript with the full-length open reading frame (clone 35-2; FIG. 2). Translation of a transcript that was truncated just downstream of the initiating AUG (clone 46-2; FIG. 2) resulted in the production of shorter polypeptides, presumably due to initiation at downstream AUGs. All of these AUGs (in both the full-length and truncated transcripts) are within acceptable Kozak sequences. However, while none of the Kozak sequences would be considered "strong", it is likely that the upstream-most AUG functions preferentially, if not exclusively, in vivo. This will have to be confirmed experimentally by the isolation and N-terminal sequence analysis of the native protein. Upstream of the long open reading frame are termination codons in all three reading frames, so that it is unlikely that initiation of the 39 kd protein occurs any further upstream. Primer extension analysis provided evidence for a relatively long 5' untranslated region of 248 nucleotides. Although most mRNAs have 5' untranslated regions of less than 100–200 nucleotides, there is a significant number that is greater than 200 nucleotides. It is of interest that there is an out-of-frame AUG followed by a termination codon just upstream of the large open reading frame (nucleotides 26–55 of the 35-2 sequence; FIG. 3). This would give rise to a 9-amino-acid peptide if it were translated. While the significance of so-called "nonfunctional" upstream AUG codons is not known, they have been found to occur in the longer 5' untranslated regions characteristic of certain proto-oncogene mRNAs.

The optimal alignment program GAP provided evidence for homology of the prokaryotic and eukaryotic sequences. GAP calculates a global similarity score based on the Needleman-Wunsch algorithm for an alignment that covers the full length of both sequences being compared. The GAP analysis shown in FIG. 6 compares the complete sequences of the phosphotriesterase (amino acids 1-365) and mouse phosphotriesterase related protein (amino acids 1-349). Another optimal alignment program BESTFIT (Genetics Computer Group, Inc., Madison, Wis.) was also used (data not shown). BESTFIT uses the Smith-Waterman algorithm to calculate the optimal local sequence similarity starting and ending anywhere in the sequences being compared. This is considered the most powerful method in the GCG software package for identifying the best region of similarity between two sequences, but it does not match the entire lengths of both sequences. Thus, in contrast to the GAP analysis (FIG. 6), which shows the full lengths of both sequences, the BESTFIT analysis did not show the first two amino acids at the N-terminus and the last two amino acids at the C-terminus of mouse phosphotriesterase related gene of the present invention (data not shown). Otherwise, the BESTFIT analysis was very similar to that obtained with GAP. In fact, the two programs found the exact same alignments for amino acids 7–346 of mouse phosphotriesterase related gene of the present invention and for amino acids 36–358 of parathion hydrolase. With BESTFIT, the similarity was 50% and the identity was 26%, with a quality score of 162.5 compared to an average quality for ten randomizations of 109.7±2.7. With GAP (FIG. 6), the similarity was 51% and the identity was 27%, with a quality score of 162.4 compared to an average quality for ten randomizations of 109.2±4.6. Based on these scores for both BESTFIT and GAP, it would appear that the prokaryotic and eukaryotic sequences are evolutionarily related. With both analyses, a region at the N-terminus of the Flavobacterium parathion hydrolase did not match well with the mouse sequence. Most of this region corresponds to a 29 amino acid leader sequence on the prokaryotic polypeptide, which is presumably required for its secretion. The absence of this signal sequence from the eukaryotic polypeptide would suggest that the protein expressed by the mouse phosphotriesterase related gene of the present invention is not secreted.

The phosphotriesterase from *Pseudomonas diminuta* (which is identical to the Flavobacterium protein) is a zinc metalloenzyme that has a broad substrate specificity, catalyzing the hydrolysis of organophosphate-triester compounds. Among the substrates of the enzyme are the insecticides parathion and paraoxon. The enzyme is known as parathion hydrolase, organophosphorous acid anhydrase, aryldialkylphosphatase, or phosphotriesterase. The native protein contains two atoms of zinc, which are required for catalytic activity. The Pseudomonas enzyme has 7 histidines (H55, H57, H123, H201, H230, H254, and H257; see FIG. 6). Based primarily on site-directed mutagenesis, there is a requirement for all of the histidines except H123 for catalytic activity. It is envisioned that H55, H57, H230, H254, and H257 coordinate with the two atoms of zinc (with H230 acting as the bridging ligand between the two zinc ions) and that H201 is the catalytic base or proton-shuttle group for the reaction. Five of the 7 histidines in the Flavobacterium/Pseudomonas protein are conserved in the mouse sequence (FIG. 6). These include the H55/H57 pair, which is within the most highly conserved region of the protein, a sequence that includes 6 contiguous identical amino acid residues. Also conserved are H201 (the putative catalytic base) and H230 (the putative bridging residue). H123 was also conserved, although this residue was found not to be required for catalytic activity. The only histidines that did not have a counterpart in the mouse sequence are the H254/H257 pair. The overall conservation of these histidines lends further support to the idea that the Flavobacterium/Pseudomonas and mouse phosphotriesterase genes are evolutionarily related.

Determination of whether the mouse phosphotriesterase related protein of the present invention has a similar range of substrates and enzymatic activities as the bacterial protein is not known. The primarily kidney and liver expression of mpr56-1 is consistent with a role for the protein in xenobiotic detoxification, however, the natural substrates for the mouse enzyme, and what (if anything) might regulate the synthesis of this protein, are also not known. As determined from an analysis of the primary sequence, the mouse phosphotriesterase related protein appears not to be secreted. If this is the case, its functions might be restricted to kidney and liver. In this context, it should be mentioned that arylesterases that degrade paraoxon have been isolated from liver microsomes and cytosol and from blood plasma of human, rabbit, and rat. These so-called paraoxonases are synthesized predominantly, if not exclusively, in the liver and have different properties from the bacterial parathion hydrolasc (phosphotriesterase). Furthermore, the human and rabbit cDNAs for serum paraoxonase/arylesterase have been isolated and characterized and were found to be unrelated to both the Flavobacterium/Pseudomonas phosphotriesterase and the mouse phosphotriesterase related gene sequence using BLASTP and FASTA similarity searches (data not shown).

The discovery of the mouse protein of the present invention predicts that similar proteins exist in humans and other mammalian species. Mouse phosphotriesterase related protein (or a similar mammalian protein) having an enzymatic activity similar to the bacterial parathion hydrolase, indicates that the purified protein has several useful applications. First, the enzyme is useful as a therapeutic or protective treatment for acute organophosphate toxicity, by intravenous infusion as the purified protein or protein encapsulated in lipid vesicles. The purified bacterial enzyme has been used in mice subjected to a toxic dose of paraoxon indicating that the addition of the bacterial parathion hydrolase above endogenous levels of serum paraoxonase has a protective effect in these animals. A mammalian counterpart for the bacterial enzyme might provide a safer or more efficacious protein for similar treatments of human patients.

Enzymatic, i.e., phosphotriesterase, activity of the mouse phosphotriesterase related protein of the present invention provides applications that would enhance the effectiveness of other types of therapy. For example, a number of therapeutic drugs either contain a phosphotriester or form a phosphotriester as part of their action. The effectiveness of such drugs might be compromised by an endogenous phosphotriesterase activity. The discovery of the eukaryotic phosphotriesterase-related protein of the present invention will allow the design of specific inhibitors of the enzyme. The use of these phosphotriesterase inhibitors as co-drugs or pro-drugs would enhance the overall therapeutic action of certain drugs. For example, the cancer chemotherapeutic agent PBI, causes phosphate alkylation of DNA followed by strand cleavage. This phosphate alkylation results in the formation of a phosphotriester, which could be reversed by an endogenous phosphotriesterase activity, decreasing the effectiveness of the treatment. Another example involves the treatment of AIDS with AZT. Lipophilic glycosyl phosphotriester derivatives of AZT are utilized because of their enhanced delivery or activity. Such derivatives may be substrates for an endogenous phosphotriesterase. If so, the inhibition of the phosphotriesterase would help to stabilize the AZT derivatives and prolong their half-lives for an enhanced long-term effectiveness. In this context, a number of different types of antisense oligonucleotide derivatives are being experimented with as therapeutic agents against the HIV virus. Because of the intrinsic instability of the phosphodiester bond, derivatives have been designed with isopropyl or methyl phosphate groups, resulting in a more stable phosphotriester bond. Again, an endogenous phosphotriesterase activity could compromise the long-term stability of these oligonucleotides either in the blood or following uptake by cells. An ability to inhibit an endogenous phosphotriesterase activity would extend the half-lives of certain drugs.

Finally, the decreased expression of the mouse phosphotriesterase related protein of the present invention seen in polycystic kidney disease and following acute renal failure, shows that gene activity, expression of the protein, or the level of a metabolite is a diagnostic marker of disease progression or of acute renal failure. For example, if the level of the protein decreases dramatically upon renal injury, a test in which the substrate for the enzyme or the product of the enzyme's action is measured in the urine is a rapid and simple measure of the degree of kidney damage and the subsequent recovery of renal function.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. DNA sequences encoding a mouse phosphotriesterase-related protein having the sequence shown in SEQ ID NO. 12.

2. The DNA of claim 1, wherein said DNA has the sequence shown in SEQ ID NO. 1.

3. A vector comprising a DNA sequence coding for a mouse phosphotriesterase-related protein and said vector is capable of replication in a host which comprises, in operable linkage:
   a) an origin of replication;
   b) a promoter; and
   c) a DNA sequence coding for said protein.

4. The vector of claim 3, wherein said DNA sequence is SEQ ID No. 1.

5. A host transformed with a recombinant DNA molecule, wherein said recombinant DNA molecule comprises a DNA sequence having the sequence of SEQ ID No. 1.

6. The host of claim 5, which is *E. coli*.

7. The host of claim 6, wherein said *E. coli* is deposited under Accession No. 69712 in the American Type Culture Collection.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1697
        ( B ) TYPE: nucleic acid
        ( C ) STRANDEDNESS: double
        ( D ) TOPOLOGY: linear ( i i ) MOLECULE TYPE:
        ( A ) DESCRIPTION: cDNA ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

```
GGCACGAGGC  GGCGCACAGC  GCGGAATGAA  GGAAGCCCCG  GAGCTGGTTA  AGTAGCTGTG      60

GACCTGGTAG  GAAAGAGAAA  ATCCCTGAGA  CACTATCAGG  AATGTCTTCC  TTAAGTGGGA     120

AAGTACAAAC  AGTTCTGGGC  CTTGTAGAAC  CCAGCCAACT  GGGACGCACC  CTGACCCACG     180

AGCATCTGAC  AATGACCTTT  GACAGTTTTT  ACTGCCCACC  TCCTCCATGC  CACGAAGTCA     240

CCTCCAAGGA  ACCTATCATG  ATGAAAAATC  TATTTTGGAT  TCAGAAAAAC  CCCTATTCCC     300

ATCGAGAGAA  CCTTCAGTTG  AATCAGGAGG  TAGGAGCCAT  AAGAGAAGAG  CTGTTGTATT     360

TCAAGGCTAA  GGGCGGAGGA  GCCTTGGTGG  AGAATACGAC  AACTGGGCTC  AGCAGGGACG     420

TGCATACGCT  GAAGTGGCTG  GCAGAGCAGA  CTGGAGTCCA  CATCATAGCT  GGAGCTGGGT     480

TTTATGTTGA  TGCAACTCAC  TCTGCAGCAA  CCAGAGCCAT  GTCAGTGGAG  CAGCTTACAG     540

ATGTCCTTAT  TAATGAAATT  CTCCATGGAG  CTGATGGCAC  CAGCATCAAG  TGTGGAGTTA     600

TTGGAGAAAT  TGGCTGCTCC  TGGCCTTTGA  CTGACAGCGA  GAGAAAGATA  CTTGAGGCTA     660

CAGCTCACGC  CCAGGCTCAG  CTTGGCTGTC  CTGTCATCAT  CCATCCTGGA  CGGAACCCAG     720
```

```
GTGCACCATT  CCAGATAATC  CGTATACTGC  AAGAAGCAGG  AGCAGACATC  TCCAAAACAG    780
TCATGTCCCA  CCTTGACAGG  ACTATATTTG  ATAAGAAAGA  GCTGCTGGAG  TTTGCTCAAC    840
TTGGCTGCTA  CTTGGAATAC  GATCTCTTTG  GTACGGAACT  CCTTAATTAC  CAGTTGAGCC    900
CAGATATTGA  TATGCCTGAT  GATAACAAAA  GAATTAGAAG  GGTCCATTTT  CTAGTGGATG    960
AGGGCTATGA  AGATCGGATT  CTCATGGCAC  ATGACATACA  CACAAAGCAT  CGGTTGATGA   1020
AGTACGGAGG  TCACGGCTAC  TCACACATCC  TTACCAACAT  TGTTCCTAAG  ATGCTCCTTA   1080
GAGGTCTGAC  TGAGAGGGTG  CTTGACAAGA  TACTCATAGA  AAACCCTAAA  CAATGGCTGA   1140
CTTTTAAATA  GGATGGCTGT  TCACGAACCC  AGACCTGGAG  GATACAATGA  GCAGAGAATA   1200
GTTGGTGATT  TCAAATCTAC  TGGAGACATT  AATCCAGTCT  ACATAGAACT  GGTGAATGGT   1260
CACTTCTCTC  CTATGAGAAG  CTGGATAACT  ACCACAGGGA  CATCTCTGGT  GGGGGCCACA   1320
GGGCTCAAGT  GAGTCCCATT  GTCTTTCCTT  AATAAAATAA  ATATTGATAA  AAGAGCATGT   1380
TTCCAAACAG  TAGTTTAAAA  CTATATCCCC  TAAGAATCAT  TTTGGATGTC  TTCCCCAACC   1440
CTGACTCTGT  GATCTGCACT  ACTTGAGAAA  AATGAAAGTG  TTTCTAGCTA  AGTTGCCCCT   1500
TCTGGAGCAA  CCTAATGTTT  CTTGTAATAT  TGATGATCCT  ACTAATTATC  CTGCTGTTCT   1560
TTAATTAATG  CTTAATGAAT  AATATGGCAT  TTTAAAATCA  CTTTTGCAAC  AAGGGAAGTT   1620
AAATTTTGAG  ACATTTTTTC  CCAAGGAGA   CTGCAATAAA  ATTACCAATT  CACAACAATA   1680
AAGAAATTTC  GAAGGTT                                                      1697
```

( 2 ) INFORMATION FOR SEQ ID NO:2:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:2:

```
GCCATAAGAG  AAGAGCTG                                                       18
```

( 2 ) INFORMATION FOR SEQ ID NO:3:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:

( C ) INDIVIDUAL ISOLATE:
                ( D ) DEVELOPMENTAL STAGE:
                ( F ) TISSUE TYPE:
                ( G ) CELL TYPE:
                ( H ) CELL LINE:

( x i ) SEQUENCE DESCRIPTION: SEQ ID NO:3:

CAAGTAGTGC AGATCACAG                                                                                    19

( 2 ) INFORMATION FOR SEQ ID NO:4:

( i ) SEQUENCE CHARACTERISTICS:
                ( A ) LENGTH: 17
                ( B ) TYPE: nucleic acid
                ( C ) STRANDEDNESS: double
                ( D ) TOPOLOGY: linear ( i i ) MOLECULE TYPE:
                ( A ) DESCRIPTION: other nucleic acid ( i i i ) HYPOTHETICAL: No ( i v ) ANTI-SENSE: No ( v i ) ORIGINAL SOURCE:
                ( B ) STRAIN:
                ( C ) INDIVIDUAL ISOLATE:
                ( D ) DEVELOPMENTAL STAGE:
                ( F ) TISSUE TYPE:
                ( G ) CELL TYPE:
                ( H ) CELL LINE:

( x i ) SEQUENCE DESCRIPTION: SEQ ID NO:4:

AGGCTCAGCT TGGCTGT                                                                                      17

( 2 ) INFORMATION FOR SEQ ID NO:5:

( i ) SEQUENCE CHARACTERISTICS:
                ( A ) LENGTH: 18
                ( B ) TYPE: nucleic acid
                ( C ) STRANDEDNESS: double
                ( D ) TOPOLOGY: linear ( i i ) MOLECULE TYPE:
                ( A ) DESCRIPTION: other nucleic acid ( i i i ) HYPOTHETICAL: No ( i v ) ANTI-SENSE: No ( v i ) ORIGINAL SOURCE:
                ( B ) STRAIN:
                ( C ) INDIVIDUAL ISOLATE:
                ( D ) DEVELOPMENTAL STAGE:
                ( F ) TISSUE TYPE:
                ( G ) CELL TYPE:
                ( H ) CELL LINE:

( x i ) SEQUENCE DESCRIPTION: SEQ ID NO:5:

CAAGTGAGTC CCATTGTC                                                                                     18

( 2 ) INFORMATION FOR SEQ ID NO:6:

( i ) SEQUENCE CHARACTERISTICS:
                ( A ) LENGTH: 16
                ( B ) TYPE: nucleic acid
                ( C ) STRANDEDNESS: double
                ( D ) TOPOLOGY: linear ( i i ) MOLECULE TYPE:
                ( A ) DESCRIPTION: other nucleic acid ( i i i ) HYPOTHETICAL: No ( i v ) ANTI-SENSE: No ( v i ) ORIGINAL SOURCE:
  ( B ) STRAIN:
  ( C ) INDIVIDUAL ISOLATE:
  ( D ) DEVELOPMENTAL STAGE:
  ( F ) TISSUE TYPE:
  ( G ) CELL TYPE:
  ( H ) CELL LINE:

( x i ) SEQUENCE DESCRIPTION: SEQ ID NO:6:

GACATCTCCA AAACAG                        16

( 2 ) INFORMATION FOR SEQ ID NO:7:

( i ) SEQUENCE CHARACTERISTICS:
  ( A ) LENGTH: 17
  ( B ) TYPE: nucleic acid
  ( C ) STRANDEDNESS: double
  ( D ) TOPOLOGY: linear ( i i ) MOLECULE TYPE:
  ( A ) DESCRIPTION: other nucleic acid ( i i i ) HYPOTHETICAL: No ( i v ) ANTI-SENSE: No ( v i ) ORIGINAL SOURCE:
  ( B ) STRAIN:
  ( C ) INDIVIDUAL ISOLATE:
  ( D ) DEVELOPMENTAL STAGE:
  ( F ) TISSUE TYPE:
  ( G ) CELL TYPE:
  ( H ) CELL LINE:

( x i ) SEQUENCE DESCRIPTION: SEQ ID NO:7:

ACAGCCAAGC TGAGCCT                       17

( 2 ) INFORMATION FOR SEQ ID NO:8:

( i ) SEQUENCE CHARACTERISTICS:
  ( A ) LENGTH: 17
  ( B ) TYPE: nucleic acid
  ( C ) STRANDEDNESS: double
  ( D ) TOPOLOGY: linear ( i i ) MOLECULE TYPE:
  ( A ) DESCRIPTION: other nucleic acid ( i i i ) HYPOTHETICAL: No ( i v ) ANTI-SENSE: No ( v i ) ORIGINAL SOURCE:
  ( B ) STRAIN:
  ( C ) INDIVIDUAL ISOLATE:
  ( D ) DEVELOPMENTAL STAGE:
  ( F ) TISSUE TYPE:
  ( G ) CELL TYPE:
  ( H ) CELL LINE:

( x i ) SEQUENCE DESCRIPTION: SEQ ID NO:8:

GTCGTATTCT CCACCAA                       17

( 2 ) INFORMATION FOR SEQ ID NO:9:

( i ) SEQUENCE CHARACTERISTICS:
  ( A ) LENGTH: 18
  ( B ) TYPE: nucleic acid
  ( C ) STRANDEDNESS: double
  ( D ) TOPOLOGY: linear ( i i ) MOLECULE TYPE:

(A) DESCRIPTION: other nucleic acid (iii) HYPOTHETICAL: No (iv) ANTI-SENSE: No (vi) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(xi) SEQUENCE DESCRIPTION: SEQ ID NO:9:

GATGAGGGCT ATGAAGAT                                                         18

(2) INFORMATION FOR SEQ ID NO:10:

(i) SEQUENCE CHARACTERISTICS:
    (A) LENGTH: 18
    (B) TYPE: nucleic acid
    (C) STRANDEDNESS: double
    (D) TOPOLOGY: linear (ii) MOLECULE TYPE:
    (A) DESCRIPTION: other nucleic acid (iii) HYPOTHETICAL: No (iv) ANTI-SENSE: No (vi) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(xi) SEQUENCE DESCRIPTION: SEQ ID NO:10:

GTATGTCATG TGCCATGA                                                         18

(2) INFORMATION FOR SEQ ID NO:11:

(i) SEQUENCE CHARACTERISTICS:
    (A) LENGTH: 21
    (B) TYPE: nucleic acid
    (C) STRANDEDNESS: double
    (D) TOPOLOGY: linear (ii) MOLECULE TYPE:
    (A) DESCRIPTION: other nucleic acid (iii) HYPOTHETICAL: No (iv) ANTI-SENSE: No (vi) ORIGINAL SOURCE:
    (B) STRAIN:
    (C) INDIVIDUAL ISOLATE:
    (D) DEVELOPMENTAL STAGE:
    (F) TISSUE TYPE:
    (G) CELL TYPE:
    (H) CELL LINE:

(xi) SEQUENCE DESCRIPTION: SEQ ID NO:11:

AAGGCCCAGA ACTGTTTGTA C                                                21

(2) INFORMATION FOR SEQ ID NO:12:

(i) SEQUENCE CHARACTERISTICS:
    (A) LENGTH: 349
    (B) TYPE: amino acid ( D ) TOPOLOGY: Linear ( i i ) MOLECULE TYPE: Protein ( i i i ) HYPOTHETICAL: No ( i v ) ANTI-SENSE: No ( v i ) ORIGINAL SOURCE:
    ( B ) STRAIN:
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:

( x i ) SEQUENCE DESCRIPTION: SEQ ID NO:12:

```
Met  Ser  Ser  Leu  Ser  Gly  Lys  Val  Gln  Thr  Val  Leu  Gly  Leu  Val
               5                        10                            15

Glu  Pro  Ser  Gln  Leu  Gly  Arg  Thr  Leu  Thr  His  Glu  His  Leu  Thr
               20                       25                            30

Met  Thr  Phe  Asp  Ser  Phe  Tyr  Cys  Pro  Pro  Pro  Pro  Cys  His  Glu
               35                       40                            45

Val  Thr  Ser  Lys  Glu  Pro  Ile  Met  Met  Lys  Asn  Leu  Phe  Trp  Ile
               50                       55                            60

Gln  Lys  Asn  Pro  Tyr  Ser  His  Arg  Glu  Asn  Leu  Gln  Leu  Asn  Gln
               65                       70                            75

Glu  Val  Gly  Ala  Ile  Arg  Glu  Glu  Leu  Leu  Tyr  Phe  Lys  Ala  Tyr
               80                       85                            90

Gly  Gly  Gly  Ala  Leu  Val  Glu  Asn  Thr  Thr  Gly  Leu  Ser  Arg
               95                       100                           105

Asp  Val  His  Thr  Leu  Lys  Trp  Leu  Ala  Glu  Gln  Thr  Gly  Val  His
               110                      115                           120

Ile  Ile  Ala  Gly  Ala  Gly  Phe  Tyr  Val  Asp  Ala  Thr  His  Ser  Ala
               125                      130                           135

Ala  Thr  Arg  Ala  Met  Ser  Val  Glu  Gln  Leu  Thr  Asp  Val  Leu  Ile
               140                      145                           150

Asn  Glu  Ile  Leu  His  Gly  Ala  Asp  Gly  Thr  Ser  Ile  Lys  Cys  Gly
               155                      160                           165

Val  Ile  Gly  Glu  Ile  Gly  Cys  Ser  Trp  Pro  Leu  Thr  Asp  Ser  Glu
               170                      175                           180

Arg  Lys  Ile  Leu  Glu  Ala  Thr  Ala  His  Ala  Gln  Ala  Gln  Leu  Gly
               185                      190                           195

Cys  Pro  Val  Ile  Ile  His  Pro  Gly  Arg  Asn  Pro  Gly  Ala  Pro  Phe
               200                      205                           210

Gln  Ile  Ile  Arg  Ile  Leu  Gln  Glu  Ala  Gly  Ala  Asp  Ile  Ser  Lys
               215                      220                           225

Thr  Val  Met  Ser  His  Leu  Asp  Arg  Thr  Ile  Phe  Asp  Lys  Lys  Glu
               230                      235                           240

Leu  Leu  Glu  Phe  Ala  Gln  Leu  Gly  Cys  Tyr  Leu  Glu  Tyr  Asp  Leu
               245                      250                           255

Phe  Gly  Thr  Glu  Leu  Leu  Asn  Tyr  Gln  Leu  Ser  Pro  Asp  Ile  Asp
               260                      265                           270

Met  Pro  Asp  Asp  Asn  Lys  Arg  Ile  Arg  Arg  Val  His  Phe  Leu  Val
               275                      280                           285

Asp  Glu  Gly  Tyr  Glu  Asp  Arg  Ile  Leu  Met  Ala  His  Asp  Ile  His
               290                      295                           300

Thr  Lys  His  Arg  Leu  Met  Lys  Tyr  Gly  Gly  His  Gly  Tyr  Ser  His
               305                      310                           315
```

-continued

| Ile | Leu | Thr | Asn | Ile 320 | Val | Pro | Lys | Met | Leu 325 | Leu | Arg | Gly | Leu | Thr 330 |
| Glu | Arg | Val | Leu | Asp 335 | Lys | Ile | Leu | Ile | Glu 340 | Asn | Pro | Lys | Gln | Trp 345 |
| Leu | Thr | Phe | Lys 349 | | | | | | | | | | | |